US007038022B1

(12) United States Patent
Evans et al.

(10) Patent No.: US 7,038,022 B1
(45) Date of Patent: May 2, 2006

(54) MULTIMERIC FORMS OF MEMBERS OF THE STEROID/THYROID SUPERFAMILY OF RECEPTORS

(75) Inventors: Ronald M. Evans, La Jolla, CA (US); Steven A. Kliewer, San Diego, CA (US); Kazuhiko Umesono, La Jolla, CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 08/464,269

(22) Filed: Jun. 5, 1995

Related U.S. Application Data

(63) Continuation of application No. 08/169,969, filed on Dec. 20, 1993, now abandoned, which is a continuation of application No. 07/803,163, filed on Dec. 6, 1991, now abandoned.

(51) Int. Cl.
*C07K 14/72* (2006.01)

(52) U.S. Cl. ........................ 530/399; 530/350; 530/358

(58) Field of Classification Search ................. 530/350, 530/399, 358
See application file for complete search history.

(56) References Cited

FOREIGN PATENT DOCUMENTS

| WO | WO 93/13129 | 7/1993 |
|---|---|---|
| WO | WO 93/15216 | 8/1993 |

OTHER PUBLICATIONS

Glass et al. 1989 Cell 59:697–708.*
Mandelsdorf et al 1990. Nature 345:224.*
Glass Endocrine Reviews 15:391–407, 1994.
Forman et al. The New Biologist 2(1990) 587–594.
Fawell et al. Cell 60(1990) 953–962.
De Luca, L. M., "Retinoid and their receptors in differentiation, embryogenesis, and neoplasia" *The FASEB Journal*, 5:2924–2933 (1991).
Kliewer et al., "Retinoid X receptor–COUP–TF interactions modulate retinoic acid signaling" *PNAS USA*, 89:1448–1452 (1992).
Tsai et al., Interactions between a DNA–Binding Transcription Factor (COUP) and a Non–DNA Binding Factor (S300–II) *Cell*, 50: 701–709 (1987).
Issemann & Green, "Activation of a member of the steroid hormone receptor superfamily by peroxisome proliferators" *Nature* 347:645–650 (1990).
Ladias and Karathanasis, "Regulation of the Apolipoprotein AI Gene by ARP–1, a Novel Member of the Steroid Receptor Superfamily" *Science* 251:561–565 (1991).
Mangelsdorf et al., "A Direct Repeat in the Cellular Retinol–Binding Protein Type II Gene Confers Differential Regulation by RXR and RAR" *Cell* 55:555–561 (1991).
Mlodzik et al., "The Drosophila seven–up Gene, a Member of the Steroid Receptor Gene Superfamily, controls Photoeceptor Cell Fates" *Cell* 60:211–224 (1990).
Miyajima et al., "Identification of two novel members of erbA superfamily by molecular cloning: the gene products of the two are highly related to each other" *Nucleic Acids Research* 16:11057–11074 (1988).
Oro et al., "Relationship between the product of the *Drosophila ultraspiracle* locus and the vertebrate retinoid×receptor" *Nature* 347:298–301 (1990).
Rivier et al., "Synthetic Competitive Antagonists of Corticotropin–Releasing Factor: Effect on ACTH Secretion in the Rat" 224:889–891 (1984).
Schüle et al., "Functinal Antagonism between Oncoprotein c–Jun and the Glucocorticoid Receptor" *Cell* 62:1217–1226 (1990).
Sladek et al., "Liver–enriched transcription factor HNF–4 is a novel member of the steroid hormone receptor superfamily" *Genes & Devel.* 4:2353–2365 (1990).
Smith and Johnson, "Single–step purification of polypeptides expressed in *Escherichia coli* as fusions with glutathione S–transferase" Gene 67:31–40 (1988).
Studier et al., "Use of T7 RNA Polymerase to Direct Expression of Cloned Genes" *Meth. Enzymol.* 185:60–89 (1990).
Umesono et al., "Direct Repeats as Selective Response Elements for the Thyroid Hormone, Retinoic Acid, and Vitamin $D_3$ Receptors" Cell 65:1255–1265 (1991).
Vaughan et al., "Detection and Purification of Inhibin Using Antisera Generated against Synthetic Peptide Fragments" *Meth. in Enzymol.* 168: 588–617 (1989).
Wang et al., "COUP transcription factor is a member of the steriod receptor superfamily" *Nature* 340:163–166 (1989).

* cited by examiner

*Primary Examiner*—Gary Kunz
*Assistant Examiner*—Robert Hayes
(74) *Attorney, Agent, or Firm*—Stephen E. Reiter; Foley & Lardner

(57) ABSTRACT

In accordance with the present invention, it has been discovered that various members of the steroid/thyroid superfamily of receptors can interact to form multimeric species comprising a complex of more than one receptor. Accordingly, the interaction of a first receptor species with a second receptor species modulates the ability of the first receptor species to trans-activate transcription of genes maintained under hormone expression control in the presence of the cognate ligand for said first receptor.

26 Claims, 8 Drawing Sheets

| Lane | 1 | 2 | 3 | 4 | 5 | 6 | 7 | 8 | 9 | 10 | 11 | 12 | |
|---|---|---|---|---|---|---|---|---|---|---|---|---|---|
| COUP-TF | + | − | + | + | − | + | + | − | + | + | + | + | |
| RXR | − | 1X | 1X | − | 2X | 2X | − | 4X | 4X | + | + | + | |
| | | | | | | | | | | − | 1X | 3X | RXR-Ab |

FIGURE 3B

| | | | | | RARab | RXRab | PI |
|---|---|---|---|---|---|---|---|
| RAR | − | − | + | + | + | + | + |
| RXR | − | + | − | + | + | + | + |
| lane | 1 | 2 | 3 | 4 | 5 | 6 | 7 |

| | TR | | VDR | | TR | VDR |
|---|---|---|---|---|---|---|
| bRXR | − | + | − | + | | |
| lane | 1 | 2 | 3 | 4 | 5 | 6 |

| | | | | | | | | | | | | |
|---|---|---|---|---|---|---|---|---|---|---|---|---|
| GR | | | | | | | | | − | − | + | + |
| VDR | | | | | − | − | + | + | | | | |
| TR | − | − | + | + | | | | | | | | |
| RXR | − | + | − | + | − | + | − | + | − | + | − | + |

SEQUENCE LISTING

```
(1) GENERAL INFORMATION:

   (iii) NUMBER OF SEQUENCES: 28


(2) INFORMATION FOR SEQ ID NO:1:

     (i) SEQUENCE CHARACTERISTICS:
          (A) LENGTH: 71 amino acids
          (B) TYPE: amino acid
          (C) STRANDEDNESS: unknown
          (D) TOPOLOGY: unknown

    (ii) MOLECULE TYPE: peptide

    (xi) SEQUENCE DESCRIPTION: SEQ ID NO:1:

Cys Xaa Xaa Cys Xaa Xaa Asp Xaa Ala Xaa Gly Xaa Tyr Xaa Xaa Xaa
1               5                   10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70


(2) INFORMATION FOR SEQ ID NO:2:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (xi) SEQUENCE DESCRIPTION: SEQ ID NO:2:

AGGTCAAGGA GGTCA                                                        15


(2) INFORMATION FOR SEQ ID NO:3:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (xi) SEQUENCE DESCRIPTION: SEQ ID NO:3:

GGGTGAATGA GGACA                                                        15


(2) INFORMATION FOR SEQ ID NO:4:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (xi) SEQUENCE DESCRIPTION: SEQ ID NO:4:

GGGTGAACGG GGGCA                                                        15
```

-continued (2) INFORMATION FOR SEQ ID NO:5:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:5:

GGTTCACGAG GTTCA 15

(2) INFORMATION FOR SEQ ID NO:6:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:6:

AGGTCACAGG AGGTCA 16

(2) INFORMATION FOR SEQ ID NO:7:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:7:

AGGTGACAGG AGGTCA 16

(2) INFORMATION FOR SEQ ID NO:8:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:8:

AGGTGACAGG AGGACA 16

(2) INFORMATION FOR SEQ ID NO:9:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:9:

GGGTTAGGGG AGGACA 16

(2) INFORMATION FOR SEQ ID NO:10:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:10:

GGGTCATTTC AGGTCC 16

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:11:

AGGTCACCAG GAGGTCA 17

(2) INFORMATION FOR SEQ ID NO:12:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:12:

AGGTGAACAG GAGGTCA 17

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:13:

GGTTCACCGA AAGTTCA 17

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:14:

GGTTCACCGA AAGTTCA 17

(2) INFORMATION FOR SEQ ID NO:15:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:15:

AGGTCACTGA CAGGGCA 17

(2) INFORMATION FOR SEQ ID NO:16:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:16:

GGGTCATTCA GAGTTCA 17

-continued (2) INFORMATION FOR SEQ ID NO:17:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:17:

AAGCTTAAGG GTTCACCGAA AGTTCACTCA GCTT 34

(2) INFORMATION FOR SEQ ID NO:18:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:18:

AAGCTTAAGG GTTCACCGAA AGTTCACTCG CATAGCTT 38

(2) INFORMATION FOR SEQ ID NO:19:

(i) SEQUENCE CHARACTERISTICS:
(A) LENGTH: 43 base pairs
(B) TYPE: nucleic acid
(C) STRANDEDNESS: single
(D) TOPOLOGY: linear (xi) SEQUENCE DESCRIPTION: SEQ ID NO:19:

AAGCTTAAGG GTTCACCGAA AGTTCACTCG CATATATTAG CTT 43

(2) INFORMATION FOR SEQ ID NO:20:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:20:

AGCTTCAGGT CAAGGTCAGA GAGCT 25

(2) INFORMATION FOR SEQ ID NO:21:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:21:

AGCTTCAGGT CAGAGGTCAG AGAGCT 26

(2) INFORMATION FOR SEQ ID NO:22:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:22:

AGCTTCAGGT CAGGAGGTCA GAGCT 25

(2) INFORMATION FOR SEQ ID NO:23:

-continued (i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:23:

AGCTTCAGGT CAAGGAGGTC AGAGAGCT 28

(2) INFORMATION FOR SEQ ID NO:24:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:24:

AGCTTCAGGT CACAGGAGGT CAGAGAGCT 29

(2) INFORMATION FOR SEQ ID NO:25:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:25:

AGCTTCAGGT CACCAGGAGG TCAGAGAGCT 30

(2) INFORMATION FOR SEQ ID NO:26:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:26:

AGCTTAAGGG TTCACCGAAA GTTCACTCGC ATAGCTGCT 39

(2) INFORMATION FOR SEQ ID NO:27:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:27:

AGCTTGGTGT CAAAGGTCAA ACTTAGCT 28

(2) INFORMATION FOR SEQ ID NO:28:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:28:

AGCTGTCACA GGTCACAGGT CACAGGTCAC AGTTCAAGCT 40

MULTIMERIC FORMS OF MEMBERS OF THE STEROID/THYROID SUPERFAMILY OF RECEPTORS

This application is a continuation of application U.S. Ser. No. 08/169,969, filed Dec. 20, 1993, now abondoned, which is a continuation of application U.S. Ser. No. 07/803,163, filed Dec. 6, 1991, now abondoned, the entire contents of which are hereby incorporated by reference herein.

FIELD OF THE INVENTION

The present invention relates to interactions between members of the steroid/thyroid superfamily of receptor proteins, novel combinations of various members of the steroid/thyroid superfamily of receptor proteins, and methods of using such combinations.

BACKGROUND OF THE INVENTION

Transcriptional regulation of development and homeostasis in complex eukaryotes, including humans and other mammals, birds, fish, insects, and the like, is controlled by a wide variety of regulatory substances, including steroid and thyroid hormones. These hormones exert potent effects on development and differentiation of phylogenetically diverse organisms. The effects of hormones are mediated by interaction with specific, high affinity binding proteins referred to as receptors.

A number of receptor proteins are known, each specific for steroid hormones [e.g., estrogens (estrogen receptor), progesterones (progesterone receptor), glucocorticoid (glucocorticoid receptor), androgens (androgen receptor), aldosterones (mineralocorticoid receptor), vitamin D (vitamin D receptor)], retinoids (e.g., retinoic acid receptor) or thyroid hormones (e.g., thyroid hormone receptor. Receptor proteins have been found to be distributed throughout the cell population of complex eukaryotes in a tissue specific fashion.

Molecular cloning studies have made it possible to demonstrate that receptors for steroid, retinoid and thyroid hormones are all structurally related and comprise a superfamily of regulatory proteins. These regulatory proteins are capable of modulating specific gene expression in response to hormone stimulation by binding directly to cis-acting elements.

An important advance in the characterization of this superfamily of regulatory proteins has been the identification of a growing list of gene products which possess the structural features of hormone receptors.

It is known that steroid or thyroid hormones, protected forms thereof, or metabolites thereof, enter cells and bind to the corresponding specific receptor protein, initiating an allosteric alteration of the protein. As a result of this alteration, the complex of receptor and hormone (or metabolite thereof) is capable of binding with high affinity to certain specific sites on chromatin.

It is also known that many of the primary effects of steroid and thyroid hormones involve increased transcription of a subset of genes in specific cell types.

A number of transcriptional control units which are responsive to members of the steroid/thyroid superfamily of receptors have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic $\alpha_{2u}$-globulin gene transcriptional control units, responsive to androgens, estrogens, thyroid hormones, and glucocorticoids.

A major obstacle to further understanding and more widespread use of the various members of the steroid/thyroid superfamily of hormone receptors has been a lack of awareness of the possible interactions of various members of the steroid/thyroid superfamily of hormone receptors, and an understanding of the implications of such interactions on the ability of members of the steroid/thyroid superfamily of hormone receptors to exert transcriptional regulation of various physiological processes.

BRIEF DESCRIPTION OF THE INVENTION

In accordance with the present invention, we have discovered that two or more members of the steroid/thyroid superfamily of receptors can combine to form multimeric species comprising a complex of more than one receptor. Accordingly, the combination of a first receptor species with a second receptor species is capable of modulating the ability of the first receptor species to trans-activate transcription of genes maintained under expression control in the presence of cognate ligand for said first receptor.

BRIEF DESCRIPTION OF THE FIGURES

FIG. 3 contains evidence of heterodimer formation between retinoic acid receptor, hereinafter referred to as RAR and RXR. Specifically.

FIG. 3B shows gel mobility shift assays using in vitro synthesized RAR and/or RXR and a labelled response element cellular retinol-binding protein type II—retinoid X response element, hereinafter referred to as (CRBP-II-RXRE).

FIG. 4 provides evidence of heterodimer formation between, RXR-thyroid hormone receptor, hereinafter referred to as TR, and RXR- vitamin D receptor , hereinafter referred as VDR. Specifically.

DETAILED DESCRIPTION OF THE INVENTION

Figure 1:
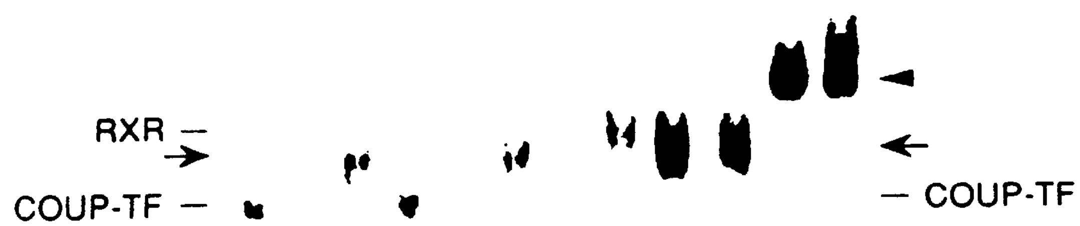
FIG. 1 shows gel mobility shift assays employing bacterially expressed chicken ovalbumin upstream promotor transcription factor, hereinafter referred to as COUP-TF and RXR, and a $^{32}$P-labelled oligonucleotide having a sequence which is recognized by the DNA-binding domains of both COUP-TF and RXR.

In accordance with the present invention, there are provided multimeric receptor species which belong to the steroid/thyroid superfamily of receptors, comprising at least the dimerization domain of at least two different members of the steroid/thyroid superfamily of receptors.

As employed herein, the term "dimerization domain" of a member of the steroid/thyroid superfamily of receptors refers to that portion of the receptor which is believed to be involved in the formation of multimeric receptor species. This domain typically comprises the carboxy-terminal portion of the receptor, i.e., that portion of a receptor which is 3' with respect to the DNA-binding domain of the receptor.

In accordance with the present invention, there are also provided combination(s) of receptors comprising at least two different members of the steroid/thyroid superfamily of receptors, wherein said receptors are associated in the form of a multimer;

wherein said combination does not include the binary combination wherein one of said members is selected from RARα, RARβ or RARγ and the other member is selected from TRα or TRβ.

Combinations contemplated by the present invention can broadly be referred to as "multimeric species", which is intended to embrace all of the various oligomeric forms in which members of the steroid/thyroid superfamily of receptors (including fragments thereof comprising the dimerization domains thereof) are capable of associating. Thus, reference to "combinations" of steroid receptors or "multimeric" forms of steroid receptors includes homodimeric combinations of a single receptor (including fragments thereof comprising the dimerization domains thereof), heterodimeric combinations of two different receptors (including fragments thereof comprising the dimerization domains thereof), homotrimeric combinations of a single receptor (including fragments thereof comprising the dimerization domains thereof), heterotrimeric combinations of two or three different receptors (including fragments thereof comprising the dimerization domains thereof), homotetrameric combinations of a single receptor (including fragments thereof comprising the dimerization domains thereof), heterotetrameric combinations of two or more different receptors (including fragments thereof comprising the dimerization domains thereof), and the like.

As employed herein, the phrase "members of the steroid/thyroid superfamily of receptors" refers to all of the various isoforms of hormone binding proteins that operate as ligand-dependent transcription factors, including members of the steroid/thyroid superfamily of receptors for which specific ligands have not yet been identified (referred to hereinafter as "orphan receptors"). Each such protein has the intrinsic ability to bind to a specific DNA sequence in a target gene. Following binding, the transcriptional activity of the gene is modulated by the presence or absence of the cognate hormone (ligand).

The DNA-binding domains of all members of this superfamily of receptors are related, consisting of 66–68 amino acid residues, and possessing about 20 invariant amino acid residues, including nine cysteines. A member of the superfamily can be identified as a protein which contains these diagnostic amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153), and the like. The highly conserved amino acids of the DNA-binding domain of members of the superfamily are as follows:

Cys-X-X-Cys-X-X-Asp*-X-Ala*-X-Gly*-X-Tyr*-X-X-X-X-Cys-X-X-Cys-Lys*-X-Phe-Phe-X-Arg*-X-X-X-X-X-X-X-X-X-(X-X-) Cys-X-X-X-X-(X-X-X-) Cys-X-X-X-Lys-X-X-Arg-X-X-Cys-X-X-Cys-Arg*-X-X-Lys*-Cys-X-X-X-Gly*-Met (SEQ ID No 1);

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors (including the various isoforms thereof) include steroid receptors such as glucocorticoid receptor, mineralocorticoid receptor, progesterone receptor, androgen receptor, vitamin $D_3$ receptor, and the like; plus retinoid receptors, such as the various isoforms of RAR (e.g., RARα, RARβ, or RARγ), the various isoforms of RXR (e.g., RXRα, RXRβ, or RXRγ), and the like; thyroid receptors, such as TRα, TRβ, and the like; as well as other gene products which, by their structure and properties, are considered to be members of the superfamily, as defined hereinabove, including the various isoforms thereof. Examples of orphan receptors include hepatocyte nuclear factor 4, hereinafter referred to as HNF4 ([see, for example, Sladek et al., in Genes & Development 4: 2353–2365 (1990)], the COUP family of receptors [see, for example, Miyajima et al., in Nucleic Acids Research 16: 11057–11074 (1988), and Wang et al., in Nature 340: 163–166 (1989)], COUP-like receptors and COUP homologs, such as those described by Mlodzik et al., in Cell 60: 211–224 (1990) and Ladias et al., in Science 251: 561–565 (1991), various isoforms of peroxisome proliferator-activated receptors hereinafter referred to as (PPARs; see, for example, Issemann, and Green, in Nature 347: 645–650 (1990)), the ultraspiracle receptor hereinafter referred to as usp [see, for example, Oro et al., in Nature 347: 298–301 (1990)], and the like. Presently preferred members of the superfamily for use in the practice of the present invention are those members which recognize "direct repeat" hormone response elements, as described in detail hereinbelow.

The formation of multimeric species can modulate the ability of the first receptor to trans-activate transcription of genes maintained under expression control in the presence of ligand for said first receptor. The actual effect on activation of transcription (i.e., enhancement or repression of transcription activity) will vary depending on the receptor species which are part of the multimeric species, as well as on the response element with which the multimeric species interacts. Thus, for example, formation of a heterodimer of RXR and RAR inhibits the ability of RXR to trans-activate RXR-mediated processes, while the same heterodimer provides enhanced trans-activation activity with respect to the ability of RAR to trans-activate RAR-mediated processes.

In accordance with another embodiment of the present invention, there is provided a method to modulate, in an expression system, the transcription activation of a gene by a first member of the steroid/thyroid superfamily of receptors, wherein the expression of said gene is maintained under the control of a hormone response element, said method comprising:

exposing said system to at least the dimerization domain of a second member of the steroid/thyroid superfamily of receptors, in an amount effective to form a multimeric complex with said first member.

Exposure of said system to at least the dimerization domain of a second member of the steroid/thyroid superfamily of receptors is accomplished by directly administering said second member (or dimerization domain thereof) to said system, or by exposing said system to compound(s) and/or condition(s) which induce expression of said second member (or dimerization domain thereof). The resulting multimeric species is effective to modulate transcription activation of said gene by the first member of the steroid/thyroid superfamily of receptors.

As employed herein, the term "modulate" refers to the ability of a given multimeric species to either enhance or repress a receptor's ability to induce transcription of a target gene, relative to such ability of said receptor in its uncomplexed state. The actual effect of multimerization on a receptor's transcription activity will vary depending on the specific receptor species which are part of the multimeric species, and on the response element with which the multimeric species interacts. Thus, for example, formation of a heterodimer of RXR and TR inhibits the ability of RXR to trans-activate RXR-mediated processes, while the same heterodimer provides enhanced trans-activation activity with respect to the ability of TR to trans-activate TR-mediated processes.

In accordance with one embodiment of the present invention, the first member of the steroid/thyroid superfamily of receptors is an isoform of RXR and the second member is selected from COUP-TF, EAR-2, PPAR, VDR, TR, RAR, or isoforms thereof. Those of skill in the art can readily identify the compound(s) and/or condition(s) which induce expression of one or more of the second members set forth above.

In accordance with this embodiment, the first member is encoded by a gene expressed in the liver, spleen, kidney, and/or small intestine. The encoded product(s) are involved in lipid metabolism and/or cholesterol homeostasis.

In accordance with another embodiment of the present invention, the first member of the steroid/thyroid superfamily of receptors is an isoform of RAR and said second member is an isoform of RXR. Those of skill in the art can readily identify the compound(s) and/or condition(s) which are capable of inducing expression of one or more isoforms of the second member (RXR) as set forth above.

In accordance with still another embodiment of the present invention, the first member of the steroid/thyroid superfamily of receptors is an isoform of TR and the second member is an isoform of RXR. Those of skill in the art can readily identify the compound(s) and/or condition(s) which are capable of inducing expression of one or more isoform of the second member (RXR) as set forth above.

In accordance with yet another embodiment of the present invention, the first member of the steroid/thyroid superfamily of receptors is VDR and the second member is an isoform of RXR. Those of skill in the art can readily identify the compound(s) and/or condition(s) which are capable of inducing expression of one or more isoform of the second member (RXR) as set forth above.

Hormone response elements contemplated for use in the practice of the present invention include naturally occurring response elements, or synthetic response elements which are composed of two or more "half sites", wherein each half site comprises the sequence

-RGBNNM-, wherein

R is selected from A or G;

B is selected from G, C, or T;

each N is independently selected from A, T, C, or G; and

M is selected from A or C;

with the proviso that at least 4 nucleotides of said -RGBNNM- sequence are identical with the nucleotides at corresponding positions of the sequence -AGGTCA-, and wherein the nucleotide spacing between each of said half-sites falls in the range of 0 up to 15 nucleotides, N.

When one of the half sites varies by 2 nucleotides from the preferred sequence of -AGGTCA-, it is preferred that the other half site of the response element be the same as, or vary from the preferred sequence by no more than 1 nucleotide. It is presently preferred that the 3'-half site (or downstream half site) of a pair of half sites vary from the preferred sequence by at most 1 nucleotide.

Since the half sites are combined in direct repeat fashion (rather than as palindromic constructs), the resulting synthetic response elements are referred to as "DR-x", wherein "DR" refers to the direct repeat nature of the association between the half sites, and "x" indicates the number of spacer nucleotides between each half site.

Exemplary response elements useful in the practice of the present invention are derived from various combinations of half sites having sequences selected from, for example, -AGGTCA-, -GGTTCA-, -GGGTTA-, -GGGTGA-, -AGGTGA-, -GGGTCA-, and the like.

The nucleotides employed in a non-zero spacer are independently selected from C, T, G, or A.

Exemplary three nucleotide spacers include -AGG-, -ATG-, -ACG-, -CGA-, and the like. Exemplary four nucleotide spacers include -CAGG-, -GGGG-, -TTTC-, and the like. Exemplary five nucleotide spacers include -CCAGG-, -ACAGG-, -CCGAA-, -CTGAC-, -TTGAC-, and the like.

Exemplary response elements contemplated by the present invention include the following DR-3 elements:

5'-AGGTCA-AGG-AGGTCA-3' (SEQ ID No. 2),

5'-GGGTGA-ATG-AGGACA-3' (SEQ ID No. 3),

5'-GGGTGA-ACG-GGGGCA-3' (SEQ ID No. 4),

5'-GGTTCA-CGA-GGTTCA-3' (SEQ ID No. 5), the following DR-4 elements:

5'-AGGTCA-CAGG-AGGTCA-3' (SEQ ID No. 6),

5'-AGGTGA-CAGG-AGGTCA-3' (SEQ ID No. 7),

5'-AGGTGA-CAGG-AGGACA-3' (SEQ ID No. 8),

5'-GGGTTA-GGGG-AGGACA-3' (SEQ ID No. 9),

5'-GGGTCA-TTTC-AGGTCC-3' (SEQ ID No. 10), the following DR-5 elements:

5'-AGGTCA-CCAGG-AGGTCA-3' (SEQ ID No. 11),

5'-AGGTGA-ACAGG-AGGTCA-3' (SEQ ID No. 12),

5'-GGTTCA-CCGAA-AGTTCA-3' (SEQ ID No. 13),

5'-GGTTCA-CCGAA-AGTTCA-3' (SEQ ID No. 14),

5'-AGGTCA-CTGAC-AGGGCA-3' (SEQ ID No. 15),

5'-GGGTCA-TTCAG-AGTTCA-3' (SEQ ID No. 16),

5'-AAGCTTAAG-GGTTCA-CCGAA-AGTTCA-CTCAGCTT-31' (SEQ ID No. 17),

5'-AAGCTTAAG-GGTTCA-CCGAA-AGTTCA-CTCGCATAGCTT-3' (SEQ ID No. 18),

5'-AAGCTTAAG-GGTTCA-CCGAA-AGTTCA-CTCGCATATATTAGCTT-3' (SEQ ID No. 19), and the like.

Presently preferred response elements contemplated for use in the practice of the present invention include:

5'-AGGTCA-AGG-AGGTCA-3' (SEQ ID No. 2),

5'-AGGTCA-CAGG-AGGTCA-3' (SEQ ID No. 6),

5'-AGGTGA-CAGG-AGGTCA-3' (SEQ ID No. 7),

5'-AGGTCA-CCAGG-AGGTCA-3' (SEQ ID No. 11),

5'-AGGTGA-ACAGG-AGGTCA-3' (SEQ ID No. 12), and the like. These are especially preferred because they represent synthetic sequences which have not been observed in nature, and thus are applicable to a wide variety of reporter systems (i e., the use of these response elements will not be limited due to any species preference based on the source of the sequence).

The invention will now be described in greater detail by reference to the following non-limiting examples.

EXAMPLES

Plasmids

Receptor expression plasmids used in the cotransfection assays are described by Mangelsdorf et al. [see Cell Vol. 66:555–561 (1991)]; and Umesono et al. [see Cell Vol. 65:1–20 (1991)].

RS-COUP-TF expression plasmid was constructed by inserting an Asp718-BamHI fragment containing the EAR-3 (i e., COUP) coding region [Miyajima et al., Nucl. Acids Res. Vol. 16:11057–11074 (1988)] into Asp718-BamHI-cut pRS expression vector.

To construct the RS-EAR-2 expression plasmid, an Eco47III-BglII fragment containing the EAR-2 coding region (Miyajima et al., supra) was blunted with Klenow and inserted into Asp718-BamHI-cut pRS, which had also been end-filled with Klenow.

All of the recombinant reporter constructs used contain either one or two copies of the indicated oligonucleotides inserted at the unique HindIII site upstream of the basal reporter construct ΔSV-CAT (Umesono et al., supra). Identity and orientation of the inserted oligonucleotides was confirmed by sequencing.

Cotransfection Assays

CV-1, HeLa, and F9 teratocarcinoma cell culture, transfections, and CAT assays were performed as previously described (Mangelsdorf et al., supra: Umesono et al., supra). In cotransfection experiments including expression plasmids RS-COUP-TF and RS-EAR-2 (see FIG. 2), cell extracts were normalized to total amount of protein for use in CAT assays, as these expression constructs were shown to severely repress expression of β-galactosidase expression vectors.

Bacterial Expression of RXR and COUP-TF hRXRα was expressed in bacteria as a fusion protein with glutathione-S-transferase using the pGEX-2T expression vector [Smith and Johnson, Gene Vol. 67:31–40 (1988)]. Purification of the fusion protein and cleavage of the glutathione-S-transferase protein from RXR with thrombin were performed as described by Mangelsdorf et al., supra.

For expression of COUP-TF in bacteria, a 1.8 kb NcoI-BamHI fragment containing the entire coding region of EAR-3 (Miyajima et al., supra) was inserted into the PET-8C expression vector [Studier et al., Methods in Enzymology 185: 60–89 (1990). BL21(DE3)plysS cells [Studier et al., supra] containing the PET-8C-COUP-TF expression construct were induced for 3 hours with 0.6 mM isopropylthiogalactoside (IPTG) and the cells subsequently lysed in lysis buffer [50 mM Tris (pH 8.0), 250 mM KCl,1 mM DTT, 1 mM PMSF, 1% Triton X-100] by freeze-thawing.

Lysates were clarified by centrifugation for 1 hour at 45,000 rpm in a Ti60 rotor (Beckman). Crude bacterial lysates containing COUP-TF were diluted in lysis buffer lacking KCl to a final concentration of 100 mM KCl and loaded on a heparin-agarose column. The column was washed with Buffer A [20 mM Tris (pH 8.0), 20% glycerol, 1 mM DTT, 1 mM PMSF], and COUP-TF subsequently eluted with Buffer A containing 800 mM KCl.

The eluted protein was dialyzed to 100 mM KCl, loaded on a MonoQ column (Pharmacia), and protein eluted with a linear salt gradient (100 mM–800 mM) in Buffer A. Fractions containing COUP-TF binding activity (eluting at 300–350 mM KCl) were pooled and aliquoted for use in gel mobility shift assays. Western blot analysis done using COUP-TF-specific antiserum confirmed that the partially-purified COUP-TF migrated upon SDS-PAGE as an ~45 kD protein.

DNA-Binding Assays

Gel mobility shift assays (20 μl) contained 10 mM Tris (pH 8.0), 40 mM KCl, 0.1% NP-40, 6% glycerol, 1 μg of poly(dI-dC), and the specific receptor species indicated in the figure legends. After 10 minutes incubation on ice, 1 ng of $^{32}$P-labeled oligonucleotide was added and the incubations were continued for an additional 10 minutes. DNA-protein complexes were resolved on 4% polyacrylamide gels in 0.5×TBE (1×TBE=90 mM Tris, 90 mM boric acid, 2 mM EDTA). Gels were dried and subjected to autoradiography at −70° C. The following oligonucleotides and their complements were $^{32}$P-labeled and used as probes:

DR-0: AGCTTC-AGGTCA-AGGTCA-GAGAGCT (SEQ ID No. 20);

DR-1: AGCTTC-AGGTCA-G-AGGTCA-GAGAGCT (SEQ ID No. 21);

DR-2: AGCTTC-AGGTCA-GG-AGGTCA-GAGCT (SEQ ID No. 22);

DR-3: AGCTTC-AGGTCA-AGG-AGGTCA-GAGAGCT (SEQ ID No. 23);

DR-4: AGCTTC-AGGTCA-CAGG-AGGTCA-GAGAGCT (SEQ ID No. 24);

DR-5: AGCTTC-AGGTCA-CCAGG-AGGTCA-GAGAGCT (SEQ ID No. 25);

βRARE: AGCTTAAG-GGTTCA-CCGAA-AGTTCA-CTCGCATAGCTGCT (SEQ ID No. 26);

COUP-TF RE: AGCTTG-GTGTCA-A-AGGTCA-AACTTAGCT (SEQ ID No. 27);

CRBPII-RXRE: AG-CTGTCA-C-AGGTCA-C-AGGTCA-C-AGGTCA-C-AGTTCA-AGCT (SEQ ID No. 28).

RXR Antiserum

A peptide corresponding to amino acids 214–229 of hRXRα was synthesized according to the technique of Rivier et al. [Science Vol. 224:889–891 (1984)]. A glycine and tyrosine were added to the carboxy terminus for coupling to human α-globulins using bisdiazotized benzadine as described by Vaughan et al., in Methods in Enzymology Vol. 168:588–617 (1989). For initial injection, Freund's complete adjuvant was mixed with an equal volume of physiological saline containing 1 mg conjugate/ml. For boosters, Freund's incomplete adjuvant was mixed with an equal volume of physiological saline containing 0.5 mg conjugate/ml. For each immunization, a rabbit received a total of 1 ml emulsion in multiple intradermal sites. Animals were injected every three weeks and bled through an ear vein seven days after each boost. Serum was collected and evaluated for receptor antibodies on the basis of Western blot analysis of hRXRα transfected COS cell extracts. The antisera used herein was collected after the sixth boost.

Example I

COUP-TF and RXR Form a Heterodimer in Vitro

Bacterial-expressed COUP-TF and RXR-glutathione-S-transferase fusion protein (RXR-GST) were mixed and the resulting complexes analyzed by gel mobility shift assays using $^{32}$P-labeled DR-1 oligonucleotide (i e., SEQ ID No. 21) as probe. The larger RXR fusion protein was used in order to maximize the migratory differences observed between the COUP-TF and RXR complexes. RXR-GST behaved identically to the nonfusion protein in terms of binding specificity with all the response elements tested, including exhibiting a marked preference for DR-1 relative to the other DRs.

Gel mobility shift assays were performed using $^{32}$P-labeled DR-1 oligonucleotide (SEQ ID No. 21) in the presence of partially-purified COUP-TF (500 ng) and increasing amounts of partially-purified RXR (1×–50 ng) as indicated in FIG. 1. Either 0.3 μl or 1 μl of RXR-specific antiserum was included in the assays (shown in lanes 11 and 12, respectively). The positions of the RXR-specific and COUP-TF-specific complexes are indicated in FIG. 1 by a plain line ("–"). The position of the COUP-TF-RXR heterodimeric complex is indicated in the Figure by an arrow, and the position of supershifted complexes is indicated in the Figure by an arrowhead. The free probe was run off the gel and is not shown.

As shown in FIG. 1 (lane 2), low amounts of RXR-GST bound only weakly to DR-1, although at higher concentrations a homodimeric complex was seen (lane 8). However, addition of increasing amounts of RXR-GST to a constant amount of COUP-TF resulted in the appearance of a complex with mobility intermediate to those formed by COUP-TF and RXR-GST alone, with the concomitant loss of the COUP-TF-specific complex (lanes 3, 6 and 9). Addition of purified GST alone did not affect the mobility of the COUP-TF complex. Formation of COUP-TF-RXR heterodimers was clearly favored relative to the formation of either homodimeric complex under the conditions employed.

Addition of RXR-specific antiserum to an assay containing both COUP-TF and RXR-GST resulted in the "supershifting" of the COUP-TF-RXR complex (lane 11). The RXR-specific antiserum did not cross-react with bacterially-expressed COUP-TF. Increasing the amount of antiserum added to the gel mobility shift assay ultimately resulted in the disruption of the COUP-TF-RXR interaction and reappearance of the COUP-TF-specific complex (lane 12). The release of COUP-TF from this complex is a likely consequence of higher amounts of the antibody stabilizing RXR homodimers.

Similar supershift data, indicating the formation of a COUP-TF-RXR heterodimeric complex, were also obtained using radiolabeled ovalbumin COUP-TF RE as probe. These results, taken together, provide compelling evidence that COUP-TF and RXR can form a highly stable heterodimeric complex in vitro.

Example II

COUP-TF Represses RXR-mediated Transactivation Through an RXR-RE

The observation that RXR can stimulate transcription through a COUP-TF recognition element suggests that COUP-TF might reciprocally activate through a CRBPII site. The in vitro binding data presented above strongly supports this proposal. However, in cotransfection analyses, it is not possible to obtain a significant COUP-TF-mediated activation of expression from reporter plasmids COUP RE2-ΔSV-CAT or CRBPII-ΔSV-CAT when tested in either F9, CV-1, or HeLa cells (FIG. 2A, lanes 9 and 10). A closely related receptor, referred to as EAR-2 (Miyajima et al., supra), also fails to activate transcription through the CRBPII reporter (FIG. 2A, lanes 11 and 12). Because COUP-TF and EAR-2 are orphan receptors, it is possible that efficient transactivation through the COUP-TF and CRBPII response elements will require addition of exogenous ligand.

Figure 2:
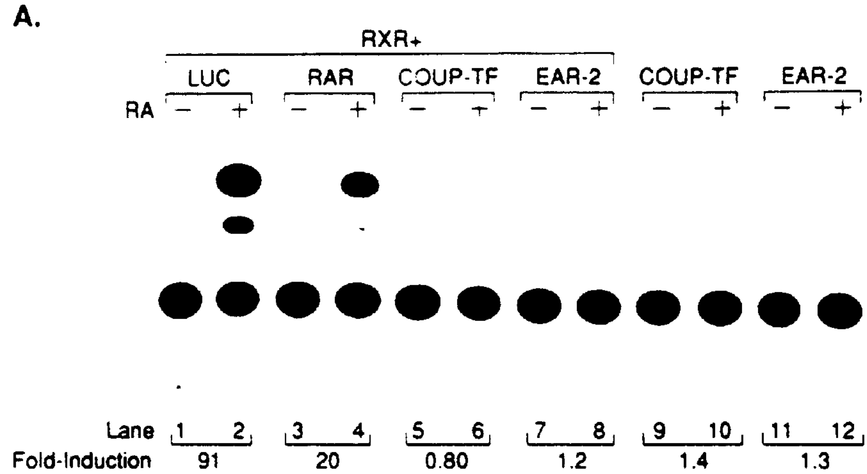
FIGS. 2A–2C summarizes the effect of COUP-TF and erbA-related gene-2, hereinafter referred to as EAR-2 on RXR-mediated transactivation studies through an RXR response element.
Figure 2:
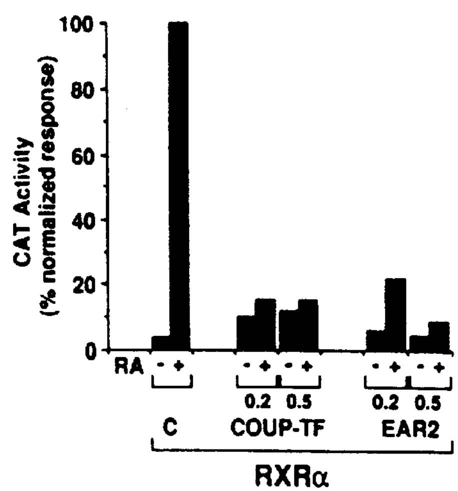
Figure 2:
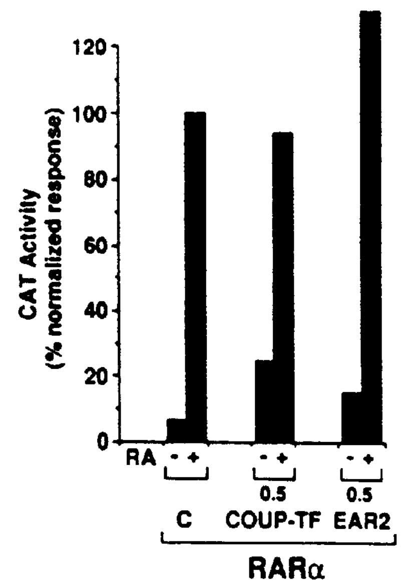

As an alternative approach, it was investigated whether COUP-TF could alter RXR-mediated induction from the CRBPII-RXRE. Accordingly, the CRBPII-CAT reporter, containing the intact promoter region of the CRBPII gene, was cotransfected into F9 cells with either RXR expression plasmid alone, or in combination with expression plasmids for either COUP-TF or EAR-2. F9 cells were cotransfected in duplicate with 3 μg the reporter pCRBPII-CAT and 1 μg of RS-hRXRα plus 0.5 μg of either the control RS-LUC (lanes 1 and 2), RS-hRARα (lanes3 and 4), RS-COUP-TF (lanes 5 and 6), or RS-EAR-2 (lanes 7 and 8). Transfection of each 10 cm plate also included 5 μg of RAS-β-galactosidase and 5.5 μg of pUC19 as carrier. Cotransfections performed with the reporter pCRBPII-CAT and either 0.5 μg RS-COUP-TF (lanes 9 and 10) or 0.5 μg of RS-EAR-2 (lanes 11 and 12) in the absence of RS-hRXRα are also shown in FIG. 2. Cells were treated with either ethanol (–) or 10 μM RA (+) for 30 hours and the cell extracts subsequently assayed for CAT activity. One set of the duplicate CAT assays is shown in the Figure.

As expected, addition of retinoic acid (RA) to cells cotransfected with CRBPII-CAT reporter and RXR expression plasmid resulted in a dramatic (approximately 90-fold) induction of CAT activity (FIG. 2A, compare lanes 1 and 2). RXR-mediated activation through the CRBPII promoter could, however, be blunted by cotransfection of RAR expression plasmid (lanes 3 and 4). Remarkably, inclusion of expression plasmids encoding either COUP-TF or EAR-2 in the cotransfection assay completely eliminated RXR-mediated transactivation through the CRBPII promoter (lanes 5–8). Thus, both COUP-TF and EAR-2 can function as potent repressors of RXR-mediated transactivation through the intact CRBPII promoter.

To demonstrate that this repression was mediated by the CRBPII element, a parallel experiment utilizing the CRPBII-ΔSV-CAT reporter was performed in CV-1 cells. CV-1 cells were cotransfected in duplicate with the reporter CRBPII-ΔSV-CAT and RS-hRXRα (1μg) in the presence of 0.5 μg RS-LUC [as a control; designated in the figure as (C)], or 0.2 and 0.5 μg of RS-COUP-TF or RS-EAR-2. Cells were treated with either ethanol (–) or 10 μM RA (+) and the cell extracts subsequently assayed for CAT activity. CAT activity is shown in FIG. 2B as percent maximal conversion where the RA-inducible activity obtained from CRBPII-ΔSV-CAT in the presence of RS-hRXRα alone is arbitrarily set at 100%.

Similar results were obtained, with both COUP-TF and EAR-2 functioning as potent inhibitors of RXR-mediated activation (FIG. 2B). As shown in FIG. 2C, the presence of either COUP-TF or EAR-2 failed to significantly reduce overall levels of RAR-mediated transactivation through the βRARE, although a slight (2- to 3-fold) increase in CAT activity in the absence of RA was reproducibly seen. CV-1 cells were cotransfected in duplicate with the reporter βRARE-ΔSV-CAT (Umesono et al., supra) and RS-RARα (1 μg) plus 0.5 μg of either RS-LUC [as a control; designated in the figure as (C)], RS-COUP-TF or RS-EAR-2. Cells were treated with either ethanol (−) or 10 μM RA (+) and the cell extracts subsequently assayed for CAT activity. CAT activity is shown in FIG. 2C as percent conversion where the RA-inducible activity obtained from βRARE-ΔSV-CAT in the presence of RS-RARα alone is arbitrarily set at 100%.

These results indicate that COUP-TF/EAR-2-mediated suppression of reporter activity is specific for RXR and its response element.

Example III

Evidence for RXR-TR and RXR-VDR Heterodimer Formation

Immunoprecipitation experiments were performed using bacterially-expressed RXR and $^{35}$S-methionine-labeled RAR synthesized in vitro. RAR, LBD, or GR RNA was prepared and subsequently translated in rabbit reticulocyte lysates as directed by the supplier (Promega). RXR was expressed in bacteria as a fusion with glutathione-S-transferase using the pGEX-2T expression vector (Pharmacia) as described by Mangelsdorf et al., supra. Immunoprecipitation reactions (20 μl) included 5 μl of [$^{35}$S]methionine-labeled receptor protein and 150 ng of either purified GST-RXR or GST alone in 20 mM Tris, pH 8.0. Proteins were incubated 20 minutes on ice prior to the addition of 5 μl of polyclonal RXR antiserum. Antigen-antibody complexes were collected by the addition of Protein A-Sepharose (Pharmacia) and the immunocomplexes washed three times with 400 μl RIPA buffer [10 mM Tris (pH 8.0), 150 mM NaCl, 1% Triton X-100, 1% sodium deoxycholate]. Immunoprecipitated complexes were resolved by SDS polyacrylamide gel electrophoresis on 10% gels which were then fixed in 30% methanol, 10% acetic acid, dried, and subjected to autoradiography. Gel retardation assays (20 μl) contained 10 mM Tris (pH 8.0), 40 mM KCl, 0.1% NP-40, 6% glycerol, 0.2 mM EDTA, 0.1 mM DTT, 0.2 μg of poly(dI-dC) and 2.5 μl of in vitro synthesized RAR and RXR proteins. When either RAR or RXR was omitted, the reaction was supplemented with the same volume of unprogrammed reticulocyte lysate. After a 10 minute incubation on ice, 1 ng of $^{32}$P-labeled oligonucleotide was added and the incubation continued for an additional 10 minutes. DNA-protein complexes were resolved on a 4% polyacrylamide gel in 0.5×TBE (1×TBE=90 mM Tris, 90 mM boric acid, 2 mM EDTA). Gels were dried and subjected to autoradiography at −70°. Gel mobility shift assays performed using Cos cell-expressed receptors were performed as described by Umesono et al., supra using whole cell extracts prepared from Cos cells transfected with either RS-hRARa, RS-hRXRa, or both expression plasmids.

Figure 3A:
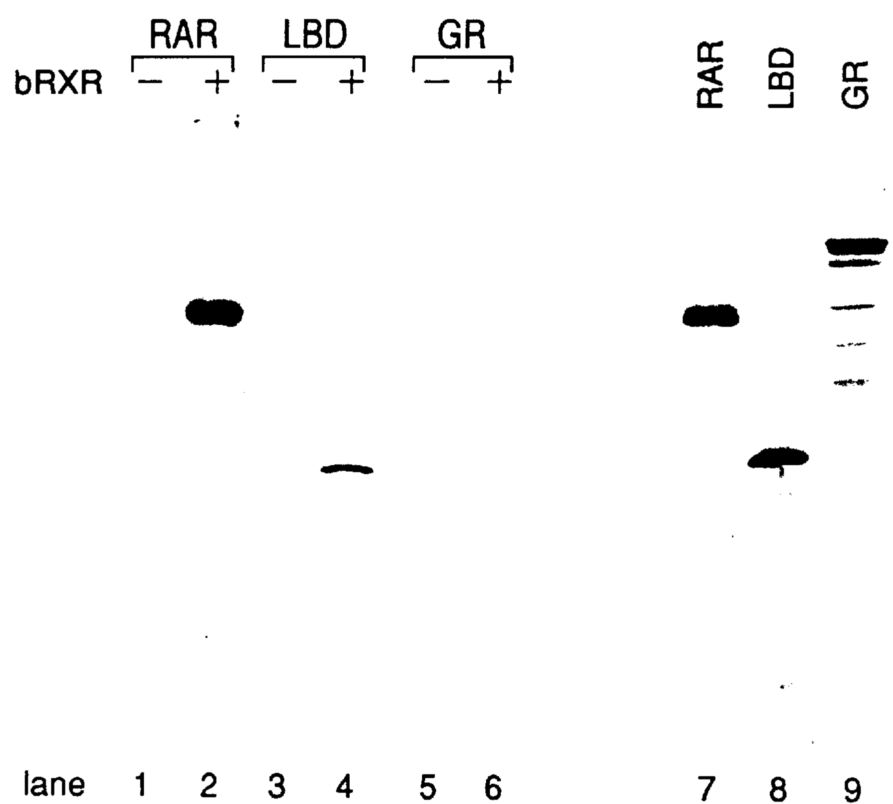
FIG. 3A shows the results of immunoprecipitation reactions between RXR and various other members of the steroid/thyroid superfamily of receptors (including fragments thereof).

As shown in FIG. 3A, preincubation of RXR and RAR followed by precipitation with anti-RXR antiserum resulted in the efficient co-precipitation of radiolabeled RAR (FIG. 3A, lane 2). In contrast, no RAR was detected when RXR was omitted from the reaction (FIG. 3A, lane 1).

Similar experiments in which RAR was replaced with radiolabeled GR failed to reveal RXR-GR interactions, demonstrating the specificity of the RAR-RXR interaction under these conditions (see FIG. 3A, lanes 5 and 6). Consistent with transfection data indicating the importance of the carboxy-terminus of RAR in mediating RAR-RXR interactions, a truncated RAR protein, consisting of only the C-terminal region of RAR, was also efficiently co-precipitated with RXR (FIG. 3A, lanes 3 and 4). Thus, RAR and RXR form a highly stable heterodimer in solution; the carboxy-terminus of RAR, containing the ligand binding and dimerization domains, is sufficient for this. interaction.

The stability of the RAR-RXR heterodimer in solution suggested that the two proteins might also interact and display novel properties when associated with DNA. To test this possibility, gel mobility shift experiments were first performed using in vitro synthesized RAR and RXR and a radiolabeled oligonucleotide encoding the CRBPII-RXRE (i e., SEQ ID No. 28). As shown in FIG. 3B, RAR synthesized in vitro bound with very low affinity to CRBPII-RXRE (lane 3). However, the affinity of binding of RAR to CRBPII-RXRE was dramatically enhanced by the addition of in vitro synthesized RXR (FIG. 3B, lane 4). In vitro synthesized RXR alone had no detectable binding activity (FIG. 3B, lane 2). Inclusion of polyclonal antisera prepared against either RAR or RXR in the reaction mixture resulted in the disruption of the protein-DNA complex and appearance of novel complexes with reduced mobility (FIG. 3B, lanes 5 and 6), indicating that both RAR and RXR were present in the complex. Thus, the RAR-RXR heterodimer is capable of interacting with high affinity with the CRBPII-RXRE.

The results of the transfection analyses presented above indicate that, under the conditions employed, the RAR-RXR heterodimer is transcriptionally inactive on the CRBPII-RXRE.

Figure 3C:
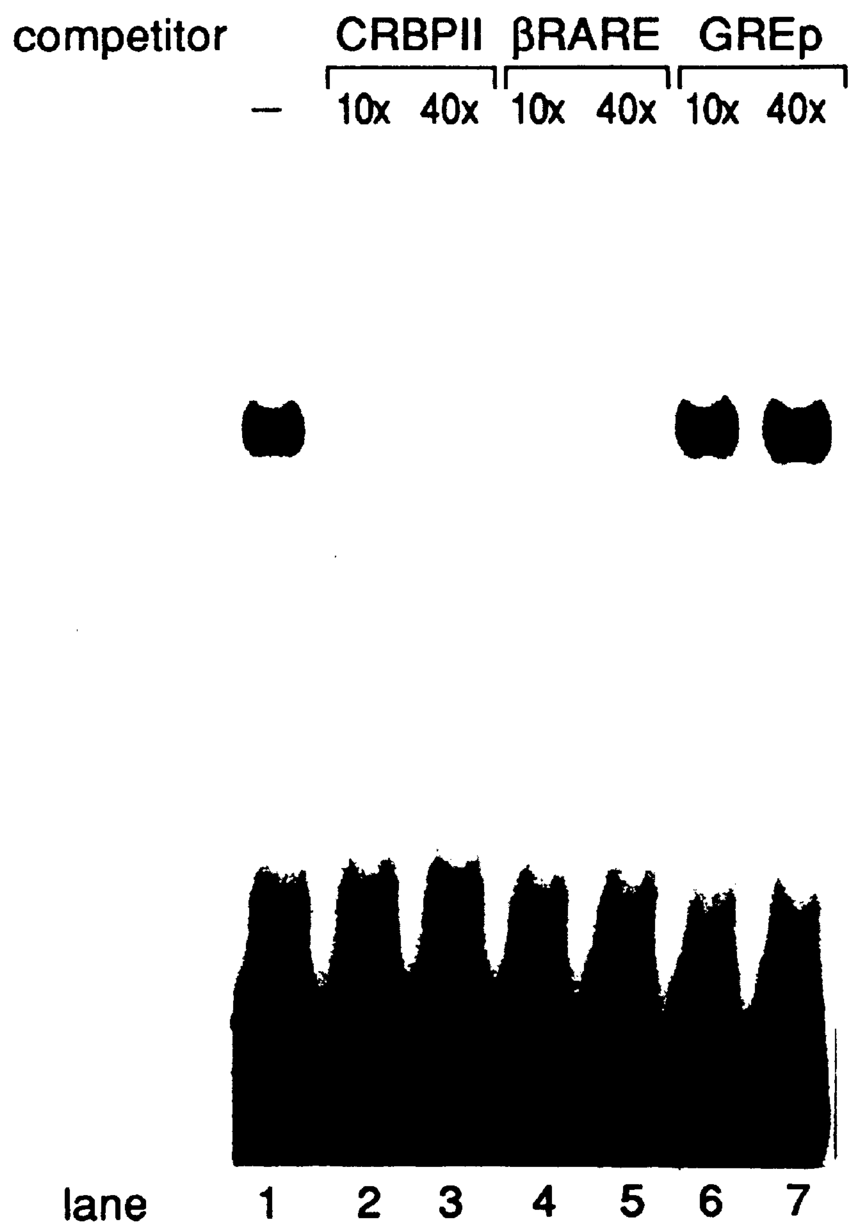
FIG. 3C shows gel mobility shift competition using a labelled response element and an excess of unlabelled competitor response element.

The specificity of the RAR-RXR interaction with DNA was next examined using unlabeled oligonucleotides as competitor. Oligonucleotides containing the CRBPII-RXRE (SEQ ID No. 28) competed efficiently for RAR-RXR heterodimer binding at a 10-fold molar excess (FIG. 3C, lane 2), whereas oligonucleotides containing an unrelated glucocorticoid response element (GRE; Schule et al., Cell 62:1217–1226 (1990)) failed to compete when used at a 40-fold molar excess relative to the radiolabeled CRBPII-RXRE (FIG. 3C, lane 7). Interestingly, oligonucleotides containing the RARE of the RARβ promoter (βRARE; SEQ ID No. 26) also competed efficiently for RAR-RXR binding to the CRBPII (FIG. 3C, lanes 4 and 5).

Figure 3D:
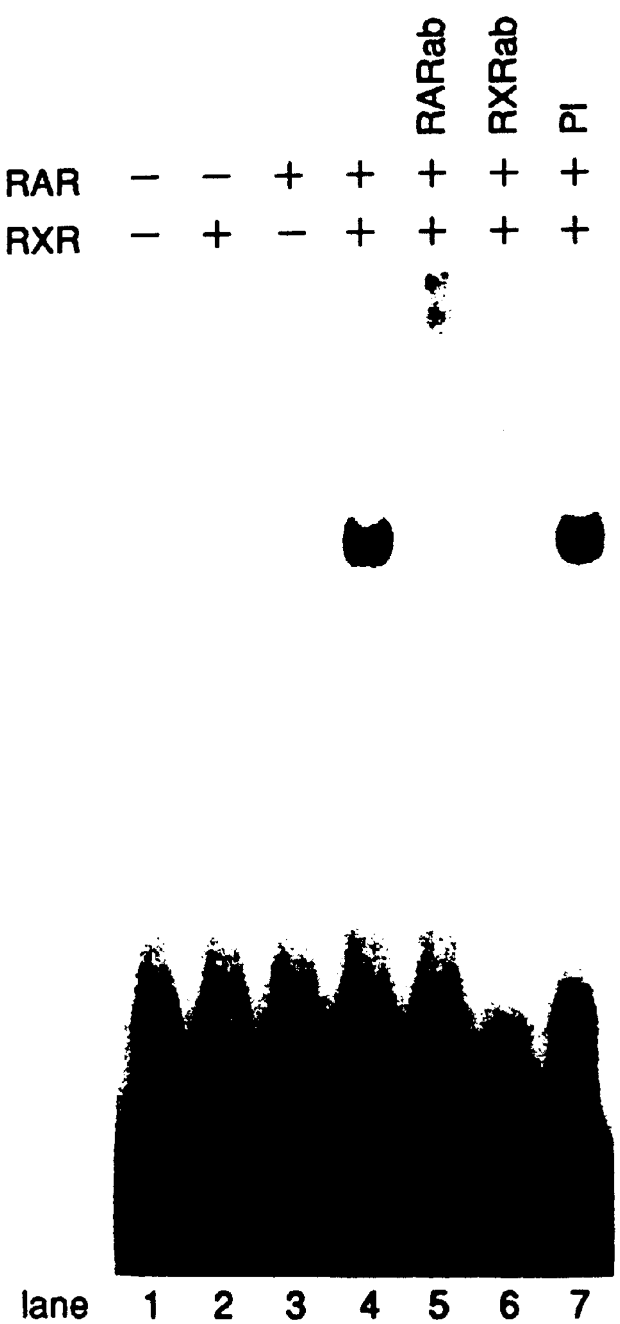
FIG. 3D shows gel mobility shift assays using in vitro synthesized RAR and/or RXR and a labelled response element beta retinoic acid response element, hereinafter referred to as (βRARE).

To further investigate this interaction of the RAR-RXR heterodimer with the βRARE (i e., SEQ ID No. 26), oligonucleotides containing the βRARE were labeled and used as probe in a gel mobility shift assay. As in the case of the CRBPII-RXRE, both in vitro synthesized RAR and RXR were required for high affinity DNA-protein interactions with the βRARE (FIG. 3D, lanes 2–4).

Figure 3E:
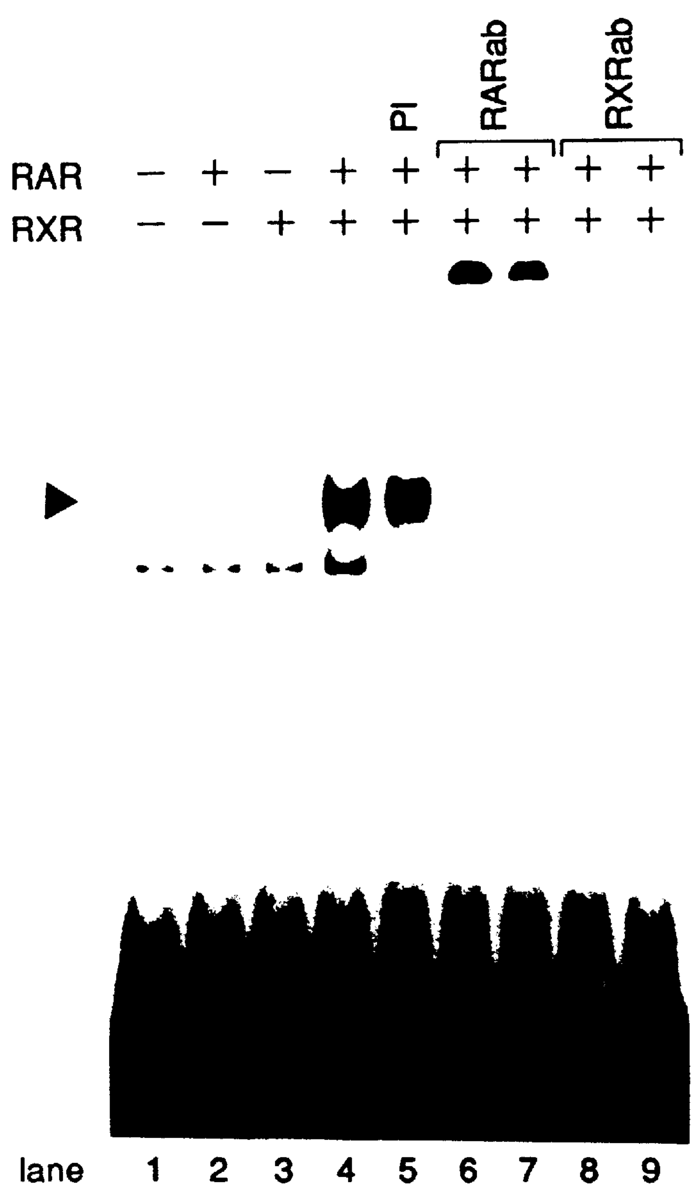
FIG. 3E shows gel mobility shift assays using labelled response element (βRARE) and whole cell extracts prepared from COS cells in which receptor is overexpressed.

Similar results indicating a requirement for the presence of both RAR and RXR for formation of a high affinity DNA-protein complex on the βRARE were obtained using whole-cell extracts prepared from Cos cells which had been transfected with either RAR alone, RXR alone, or both RAR and RXR (FIG. 3E). Taken together, these results demonstrate that RXR dramatically enhances the binding affinity of RAR to a strong retinoic acid response element, and that the RAR-RXR complex is likely to be present in vivo.

Figures 4A, 4B:
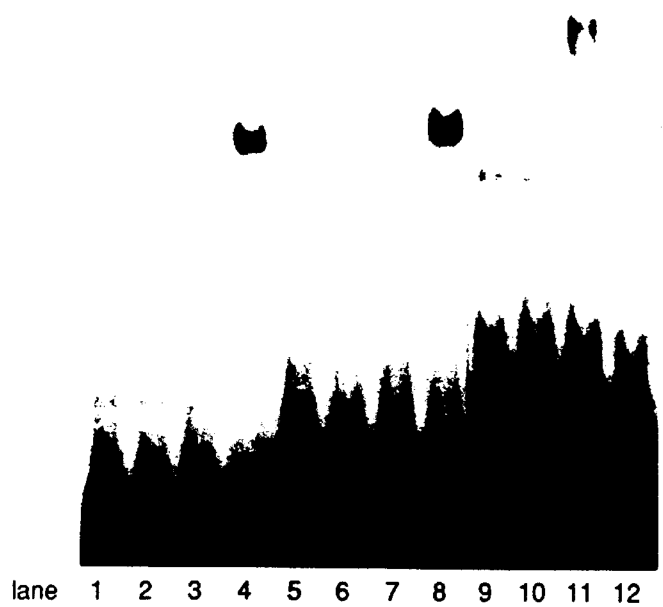
FIG. 4A shows the results of immunoprecipitation reactions between RXR and TR or VDR.
FIG. 4B shows gels mobility shift assays using in vitro synthesized RXR, TR, VDR, and GR glucocorticoid receptor, hereinafter referred to as (as noted) and labelled oligonucleotides encoding various response elements.

Similarly, in immunoprecipitation experiments, in vitro synthesized thyroid receptor-beta (TRβ) and vitamin D receptor (VDR) were found to co-precipitate with bacterially-expressed RXR (FIG. 4A, lanes 1–6). The interactions of these receptors with RXR were also manifest at the level of DNA binding: in vitro synthesized RXR was shown to dramatically enhance TRβ and VDR binding to the MLV-LTR TRE. (Umesono et al., supra) and osteopontin VDRE (Umesono et al., supra), respectively (FIG. 4B, lanes 1–8).

Taken together, these data strongly suggest a central role for members of the steroid/thyroid superfamily of receptors, such as RXR, in modulating the hormonal responses conferred via the RAR, TR, and VDR.

While the invention has been described in detail with reference to certain preferred embodiments thereof, it will be understood that modifications and variations are within the spirit and scope of that which is described and claimed.

That which is claimed is:

1. A dimeric receptor comprising one member selected from isoforms of RXR and one different member of the steroid/thyroid superfamily of receptors, wherein said members are associated in the form of a dimer.

2. A receptor according to claim 1, wherein said isoform of RXR is RXRα and said different member is selected from the group consisting of RXRβ and RXRγ.

3. A dimeric receptor according to claim 1 wherein said dimer is characterized by the ability to stably form in the absence of nucleic acid response elements therefor.

4. A dimeric receptor according to claim 1 wherein said dimer is characterized by the ability to modulate expression from direct repeat nucleic acid response elements.

5. A receptor according to claim 1, wherein said isoform of RXR is selected from the group consisting of RXRα, RXRβ, and RXRγ.

6. A receptor according to claim 5, wherein said different member is selected from the group consisting of COUP-TF, PPAR, and EAR-2.

7. A receptor according to claim 6 wherein said different member is PPAR.

8. A receptor according to claim 5, wherein said different member is VDR.

9. A receptor according to claim 5, wherein said different member is selected from the group consisting of TRα and TRβ.

10. A receptor according to claim 5, wherein said different member is selected from the group consisting of RARα, RARβ, and RARγ.

11. A receptor according to claim 10 wherein said different member is RARα.

12. A receptor according to claim 10 wherein said different member is RARγ.

13. A receptor according to claim 5 wherein said isoform of RXR is RXRα.

14. A receptor according to claim 13 wherein said different member is PPAR.

15. A receptor according to claim 13 wherein said different member is VDR.

16. A receptor according to claim 13 wherein said different member is TRα or TRβ.

17. A receptor according to claim 13 wherein said different member is RARα.

18. A receptor according to claim 13 wherein said different member is RARγ.

19. A dimeric receptor comprising one isoform of RXR and at least the dimerization domain of a different member of the steroid/thyroid hormone superfamily of receptors.

20. A dimeric receptor according to claim 19 wherein said dimeric receptor is characterized by the ability to stably form in the absence of nucleic acid response elements therefor.

21. A dimeric receptor according to claim 19 wherein said dimeric receptor is characterized by the ability to modulate expression from direct repeat nucleic acid response elements.

22. A dimeric receptor comprising at least the dimerization domain of one isoform of RXR and a different member of the steroid/thyroid hormone superfamily of receptors.

23. A dimeric receptor according to claim 22 wherein said dimeric receptor is characterized by the ability to stably form in the absence of nucleic acid response elements therefor.

24. A dimeric receptor according to claim 23 wherein said dimer is further characterized by the ability to modulate the trans-activation activity of said different member of the steroid/thyroid hormone superfamily of receptors in the presence of ligand for said different member, but in the absence of ligand for said isoform of RXR.

25. A dimeric receptor according to claim 24 wherein said dimer is further characterized by the ability to enhance the binding of said dimer to a response element for said different member of the steroid/thyroid hormone superfamily of receptors, relative to the binding of said different member to said response element when said different member is not associated with said dimerization domain.

26. A dimeric receptor according to claim 22 wherein said dimeric receptor is characterized by the ability to modulate expression from direct repeat nucleic acid response elements.

* * * * *